US012635919B2

(12) United States Patent
Seo et al.

(10) Patent No.: US 12,635,919 B2
(45) Date of Patent: May 26, 2026

(54) MULTI-CHANNEL PULSE OXIMETER SYSTEM

(71) Applicant: Medicalsolutionsystem, Gimhae City (KR)

(72) Inventors: JoonMo Seo, Busan (KR); Minsoo Kang, Busan (KR)

(73) Assignee: Medicalsolutionsystem, Gimhae city (KR)

( * ) Notice: Subject to any disclaimer, the term of this patent is extended or adjusted under 35 U.S.C. 154(b) by 376 days.

(21) Appl. No.: 18/365,672

(22) Filed: Aug. 4, 2023

(65) Prior Publication Data

US 2024/0350042 A1 Oct. 24, 2024

(30) Foreign Application Priority Data

Apr. 22, 2023 (KR) ........................ 10-2023-0053016

(51) Int. Cl.
*A61B 5/1455* (2006.01)
*A61B 5/00* (2006.01)
*A61B 5/026* (2006.01)

(52) U.S. Cl.
CPC ........ *A61B 5/14551* (2013.01); *A61B 5/0261* (2013.01); *A61B 5/6816* (2013.01); *A61B 5/6826* (2013.01); *A61B 5/6829* (2013.01)

(58) Field of Classification Search
CPC . A61B 5/14551; A61B 5/0261; A61B 5/6816; A61B 5/6826; A61B 5/6829; A61B 5/02007; A61B 5/02416; A61B 5/6838; A61B 5/14552
See application file for complete search history.

(56) References Cited

U.S. PATENT DOCUMENTS

| | | | |
|---|---|---|---|
| 2009/0149764 A1* | 6/2009 | Semler ................. | A61B 5/6838 |
| | | | 600/504 |
| 2017/0014081 A1* | 1/2017 | Schipper .............. | A61B 5/6826 |
| 2019/0060568 A1* | 2/2019 | Newberry ........... | A61M 5/1723 |

FOREIGN PATENT DOCUMENTS

KR     20190047808 A     5/2019

OTHER PUBLICATIONS

Michael Bentham, Gerard Stansby, and John Allen, "Innovative Multi-Site Photoplethysmography Analysis for Quantifying Pulse Amplitude and Timing Variability Characteristics in Peripheral Arterial Disease", Sep. 17, 2018, Diseases 2018, 6, 81 (Year: 2018).*

* cited by examiner

*Primary Examiner* — Abid A Mustansir

(74) *Attorney, Agent, or Firm* — STIP Law Group, LLC

(57) ABSTRACT

A multi-channel pulse oximeter system is proposed. The system includes a measurement part for measuring PPG signals in a light transmission method in six places on a human body, including both earlobes, both fingers, and both feet, an analysis part for comparatively analyzing the six PPG signals measured by the measurement part, and a result provision part for providing analysis results of the analysis part, wherein the measurement part is configured to include first and second measurement parts respectively mounted on both of the earlobes of the human body, third and fourth measurement parts respectively mounted on a distal end of any one of left fingers and a distal end of any one of right fingers of the human body, and fifth and sixth measurement parts respectively mounted on a left toe and a right toe of the human body, the first to sixth measurement parts measuring the PPG signals.

8 Claims, 4 Drawing Sheets

100 multi-channel pulse oximeter system measurement part —110 analysis part —120 result provision part —130

[FIG. 1]
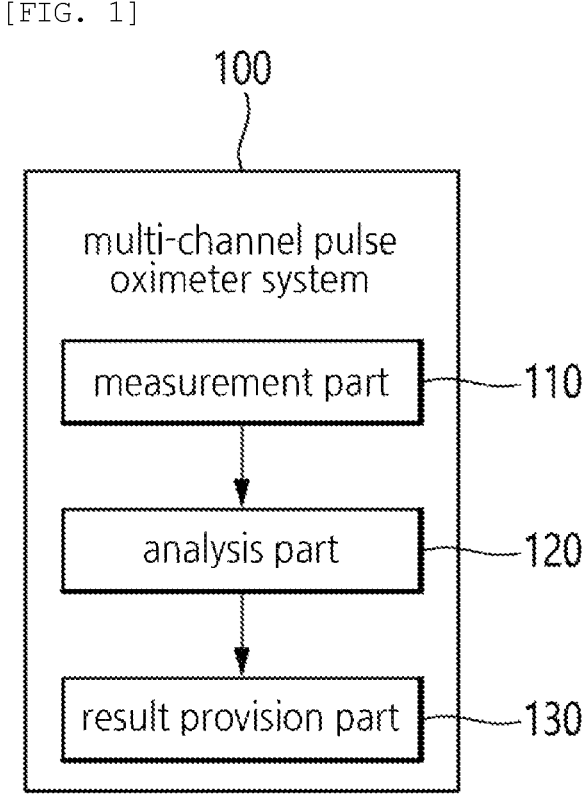
[FIG. 2]
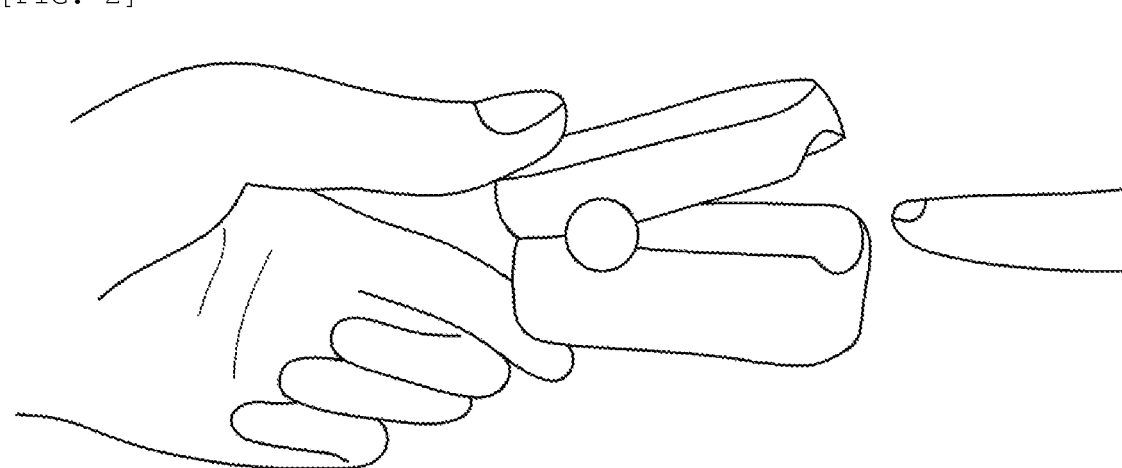

[FIG. 3]
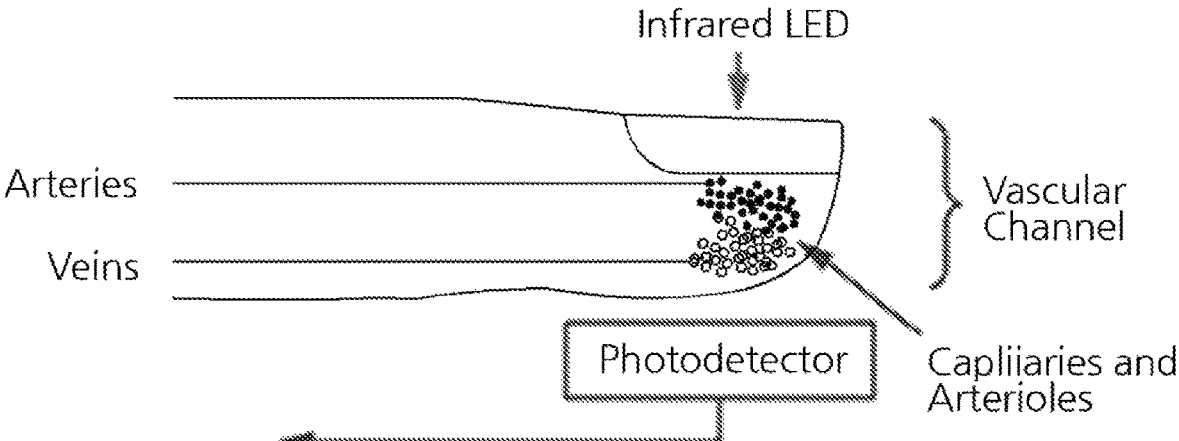
[FIG. 4]
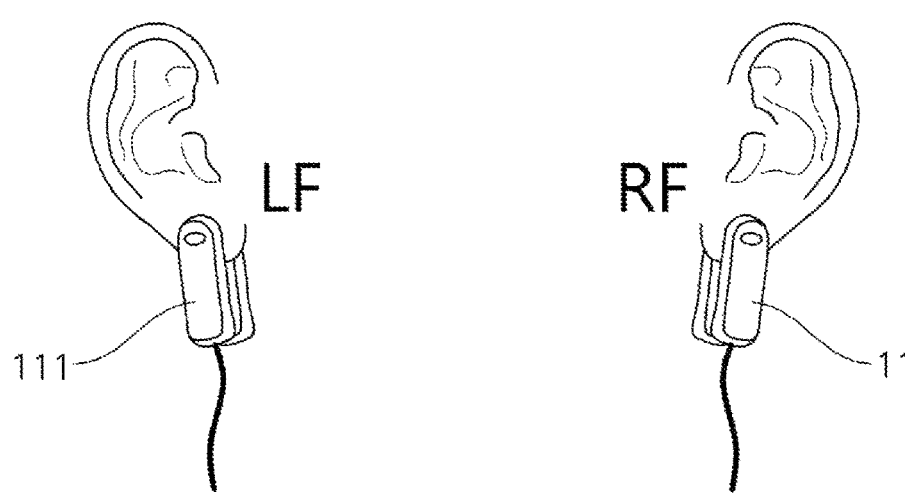

[FIG. 5]
113
114
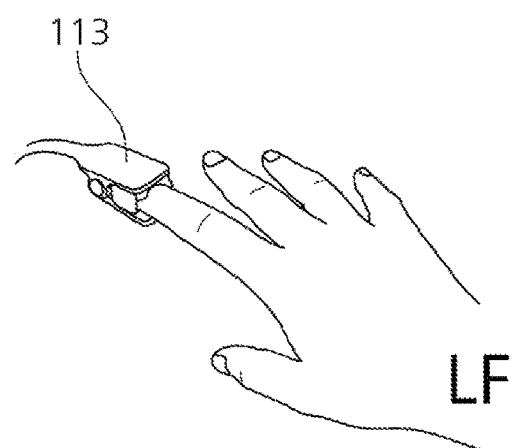 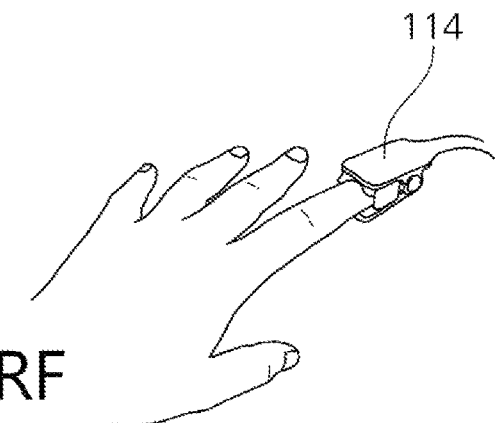
LF    RF
[FIG. 6]
115
116
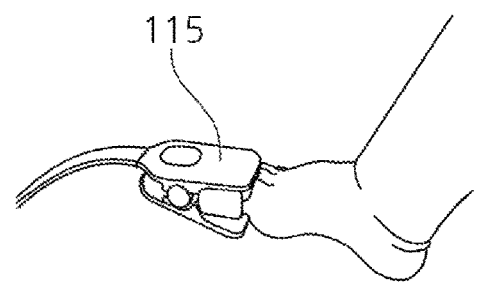 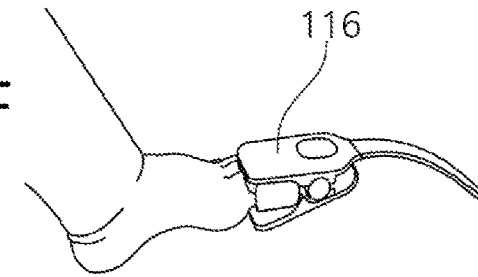
LF    RF

[FIG. 7]
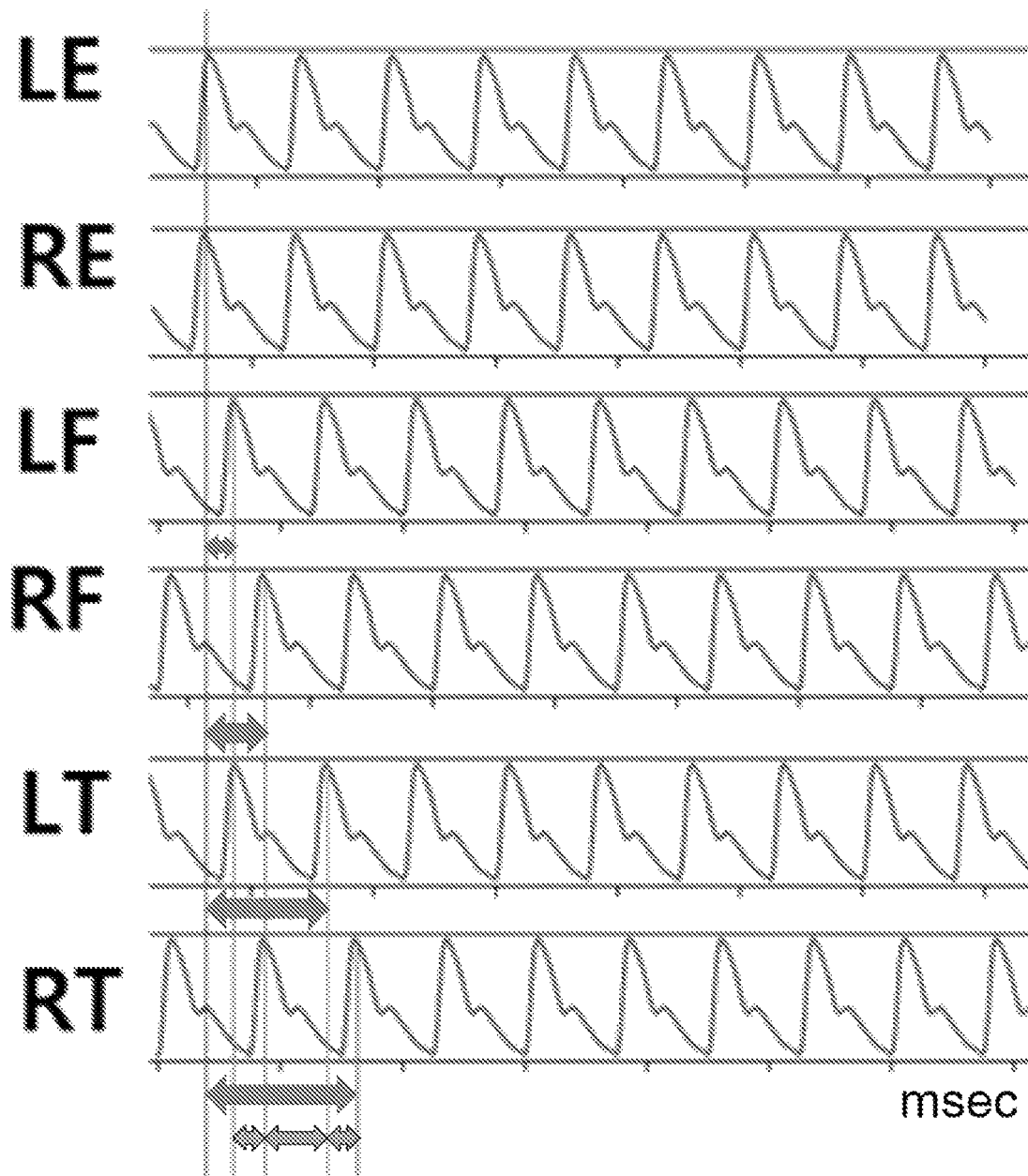

MULTI-CHANNEL PULSE OXIMETER SYSTEM

CROSS REFERENCE TO RELATED APPLICATION

The present application claims priority to Korean Patent Application No. 10-2023-0053016, filed on Apr. 22, 2023, the entire contents of which is incorporated herein for all purposes by this reference.

BACKGROUND OF THE INVENTION

Field of the Invention

The present disclosure relates to a pulse oximeter system and, more particularly, to a multi-channel pulse oximeter system for measuring and comparatively analyzing photoplethysmography (PPG) signals from various parts of a human body.

Description of the Related Art

The contents described in this section simply provide background information on an exemplary embodiment of the present disclosure, and do not constitute the related art.

Oxygen saturation test methods include an invasive method for testing arterial blood gas, and a non-invasive method for testing oxygen saturation through an oxygen saturation measuring device (i.e., a pulse oximeter). Oxygen saturation measurement using the pulse oximeter is to express, as a percentage (%), an actual binding ratio of hemoglobin and oxygen in red blood cells. In general, a normal range of oxygen saturation is 97 to 100%, and when oxygen saturation is less than 90%, hypoxemia is suspected.

Hemoglobin in red blood cells serves to transport oxygen by combining with the oxygen. The Hemoglobin combined with oxygen has properties of absorbing infrared rays (at 940 nm) better, and reduced hemoglobin not combined with oxygen has properties of absorbing light from a red light source (at 660 nm) better. In accordance with the use of these properties, when there is sufficient oxygen in the blood, the hemoglobin combined with oxygen is relatively abundant and most of infrared rays are absorbed while passing through blood vessels, whereby the infrared rays are not detected by a detector.

In general, oxygen saturation is measured by attaching a sensor part of a measuring device, provided with a light emission part and a light reception part sensor, to a fingertip. However, this method of measuring the oxygen saturation at the fingertip is limited to a specific finger, and has limitations in representing a state of the entire body.

Meanwhile, as the related art regarding the present disclosure, Korea Patent Application Publication No. 10-2019-0047808 (Invention title: MANAGEMENT SYSTEM AND METHOD OF PULSE OXIMETER, Publication Date: May 9, 2019), etc. have been disclosed.

The above-described background art is technical information that an inventor possessed for derivation of the present disclosure or acquired in a derivation process of the present disclosure, and is not necessarily known technology disclosed to the general public prior to filing the embodiment of the present disclosure.

SUMMARY OF THE INVENTION

The present disclosure is proposed to solve the above-described problems of the previously proposed methods, and an objective of the present disclosure is to provide a multi-channel pulse oximeter system that may measure PPG signals in six places on a human body, including both earlobes, both fingers, and both feet, in a light transmission method, comparatively analyze waveforms of the measured six PPG signals, and analyze a blood vessel state and blood circulation for each part of the body.

In addition, another objective of the present disclosure is to provide a multi-channel pulse oximeter system that may measure and monitor blood circulation states of a diabetic patient whose blood circulation of the extremities is problematic by analyzing degrees of time delay between the measured six PPG signals, prevent varicose veins by measuring blood circulation speeds of the lower extremities, and be utilized in diagnosis of orthostatic hypotension by measuring and analyzing the six PPG signals according to condition changes.

However, the technical problems to be solved by the present disclosure are not limited to the technical problems as described above, and other technical problems may exist. Even though not explicitly mentioned, the present disclosure naturally includes other objectives or effects, which may be identifiable from the problem solutions or embodiments.

According to features of the present disclosure for achieving the above objectives, there is provided a multi-channel pulse oximeter system including: a measurement part for measuring PPG signals in a light transmission method in six places on a human body, including both earlobes, both fingers, and both feet; an analysis part for comparatively analyzing the six PPG signals measured by the measurement part; and a result provision part for providing analysis results of the analysis part, wherein the measurement part is configured to include: a first measurement part and a second measurement part respectively mounted on both of the earlobes of the human body and measuring the PPG signals; a third measurement part and a fourth measurement part respectively mounted on a distal end of any one of left fingers and a distal end of any one of right fingers of the human body and measuring the PPG signals; and a fifth measurement part and a sixth measurement part respectively mounted on a left toe and a right toe of the human body and measuring the PPG signals.

Preferably, the first measurement part and the second measurement part may be configured in a form of a clip to be mountable on the respective earlobes.

Preferably, the fifth measurement part and the sixth measurement part may be configured in a form of a large clip to be mountable to respective toe parts of the human body.

Preferably, the analysis part may comparatively analyze waveforms of the six PPG signals measured by the first measurement part to the sixth measurement part, and analyze a blood vessel state and blood circulation for each part of the human body.

More preferably, the analysis part may analyze degrees of time delay between the waveforms of the PPG signals measured by the first measurement part to the sixth measurement part, and measure blood circulation states of a patient whose blood circulation of extremities is problematic.

Even more preferably, the result provision part may provide a blood circulation score obtained by scoring the patient's blood circulation states measured by the analysis part.

More preferably, the analysis part may compare PPG waveforms measured by the fifth measurement part and the sixth measurement part with PPG waveforms measured by the first measurement part to the fourth measurement part, analyze the degrees of time delay, and measure blood circulation speeds of lower extremities.

Even more preferably, the result provision part may calculate and provide a varicose veins index by using the blood circulation speeds of the lower extremities measured by the analysis part.

According to the present disclosure, the proposed multi-channel pulse oximeter system may measure PPG signals in six places on a human body, including both earlobes, both fingers, and both feet, in the light transmission method, comparatively analyze the waveforms of the measured six PPG signals, and analyze the blood vessel state and blood circulation for each part of the body.

In addition, according to the present disclosure, the proposed multi-channel pulse oximeter system may measure and monitor the blood circulation states of the diabetic patient whose blood circulation of the extremities is problematic by analyzing the degrees of time delay between the measured six PPG signals, prevent varicose veins by measuring the blood circulation speeds of the lower extremities, and be utilized in the diagnosis of orthostatic hypotension by measuring and analyzing the six PPG signals according to condition changes.

In addition, the various and advantageous strong points and effects of the present disclosure are not limited to the above-described contents, and will be more easily understood in the process of describing the specific embodiments of the present disclosure.

BRIEF DESCRIPTION OF THE DRAWINGS

FIG. 1 is a view illustrating a configuration of a multi-channel pulse oximeter system according to an exemplary embodiment of the present disclosure.

FIG. 2 is a view illustrating, as an example, an image in which a measurement part is mounted on a fingertip in the multi-channel pulse oximeter system according to the exemplary embodiment of the present disclosure.

FIG. 3 is a view illustrating a process by which the measurement part measures a PPG signal in a light transmission method in the multi-channel pulse oximeter system according to the exemplary embodiment of the present disclosure.

FIG. 4 is a view illustrating, as an example, an image in which a first measurement part and a second measurement part are mounted on respective earlobes in the multi-channel pulse oximeter system according to the exemplary embodiment of the present disclosure.

FIG. 5 is a view illustrating, as an example, an image in which a third measurement part and a fourth measurement part are mounted on respective fingertips in the multi-channel pulse oximeter system according to the exemplary embodiment of the present disclosure.

FIG. 6 is a view illustrating, as an example, an image in which a fifth measurement part and a sixth measurement part are mounted on respective toes in the multi-channel pulse oximeter system according to the exemplary embodiment of the present disclosure.

FIG. 7 is a view illustrating a process by which an analysis part performs a comparative analysis of the PPG signals in the multi-channel pulse oximeter system according to the exemplary embodiment of the present disclosure.

DETAILED DESCRIPTION OF THE INVENTION

Hereinafter, exemplary embodiments of the present disclosure will be described in detail with reference to the accompanying drawings so that those skilled in the art may easily implement the present disclosure. However, the present disclosure is not limited to the exemplary embodiments described herein and may be embodied in many different forms. In addition, in order to clearly describe the present disclosure in the drawings, parts irrelevant to the description are omitted, and similar reference numerals designate similar components throughout the specification.

Throughout the specification, when a part is said to be "connected" to another part, an expression such as "connected" is intended to include not only "directly connected" but also "indirectly connected" having a different component disposed between the two parts. In addition, it will be further understood that, when a part is said to "include" or "comprise" a certain component, it means that it may further include or comprise other components, but does not exclude other components unless the context clearly indicates otherwise, and does not preclude the presence or addition of one or more other features, integers, steps, operations, elements, components, and/or combinations thereof.

The following exemplary embodiments are detailed descriptions for better understanding of the present disclosure, and do not limit the scope of the present disclosure. Therefore, embodiments of the same scope that perform the same functions as those of the present disclosure will also fall within the scope of the present disclosure.

In addition, each component, process, progress, method, or the like included in each exemplary embodiment of the present disclosure may be shared within a range that does not contradict each other technically.

In addition, in the present disclosure, some of the operations or functions described as being performed by a terminal, apparatus, or device may be performed instead by a server connected to the terminal, apparatus, or device. Likewise, some of the operations or functions described as being performed by the server may also be performed by the terminal, apparatus, or device connected to the corresponding server.

In particular, a means for executing a system according to each exemplary embodiment of the present disclosure may be an application or a web server, and a terminal, which is a means for reading a recording medium on which the application or web server is recorded, may include not only a general PC such as a general desktop or laptop computer, but also a mobile terminal such as a smartphone and a tablet PC.

Hereinafter, exemplary embodiments of the present disclosure will be described in detail with reference to the accompanying drawings.

FIG. 1 is a view illustrating a configuration of a multi-channel pulse oximeter system 100 according to an exemplary embodiment of the present disclosure. As shown in FIG. 1, the multi-channel pulse oximeter system 100 according to the exemplary embodiment of the present disclosure may be configured to include a measurement part 110, an analysis part 120, and a result provision part 130.

The measurement part 110 may measure PPG signals in a light transmission method in six places on a human body, including both earlobes, both fingers, and both feet. In the present disclosure, the PPG signals may be measured in the six places on the human body by configuring a measurement part 110 for each of six channels. In this case, the PPG signals are measured in the light transmission method so that highly reliable and accurate biometric information may be collected.

FIG. 2 is a view illustrating, as an example, an image in which a measurement part 110 is mounted on a fingertip in the multi-channel pulse oximeter system 100 according to the exemplary embodiment of the present disclosure. As shown in FIG. 2, the measurement part 110 of the multi-channel pulse oximeter system 100 according to the exemplary embodiment of the present disclosure may be mounted on a body extremity or the like in a form of a clip.

FIG. 3 is a view illustrating a process by which the measurement part 110 measures a PPG signal in the light transmission method in the multi-channel pulse oximeter system 100 according to the exemplary embodiment of the present disclosure. As shown in FIG. 3, in the multi-channel pulse oximeter system 100 according to the exemplary embodiment of the present disclosure, a part of a human body, such as a fingertip, is placed between a light emitting part (i.e., an infrared LED) and a light receiving part (i.e., a photodetector), so that the PPG signal may be measured by using information of light transmitted through the human body. As such, by measuring the PPG signal in the highly accurate light transmission method, a reliable information analysis to be applicable to medical diagnosis may be performed.

FIG. 4 is a view illustrating, as an example, an image in which a first measurement part 111 and a second measurement part 112 are mounted on respective earlobes in the multi-channel pulse oximeter system 100 according to the exemplary embodiment of the present disclosure. FIG. 5 is a view illustrating, as an example, an image in which a third measurement part 113 and a fourth measurement part 114 are mounted on respective fingertips in the multi-channel pulse oximeter system 100 according to the exemplary embodiment of the present disclosure. FIG. 6 is a view illustrating, as an example, an image in which a fifth measurement part 115 and a sixth measurement part 116 are mounted on respective toes in the multi-channel pulse oximeter system 100 according to the exemplary embodiment of the present disclosure. That is, as shown in FIGS. 4 to 6, the measurement part 110 of the multi-channel pulse oximeter system 100 according to the exemplary embodiment of the present disclosure may be configured to include the first measurement part 111, the second measurement part 112, the third measurement part 113, the fourth measurement part 114, the fifth measurement part 115, and the sixth measurement part 116.

The first measurement part 111 and the second measurement part 112 may be respectively mounted on both earlobes of a human body and measure PPG signals. More specifically, the first measurement part 111 and the second measurement part 112 may be configured in the form of a clip so as to be mountable to the respective earlobes. That is, as shown in FIG. 4, the first measurement part 111 and the second measurement part 112 in the form of the clip may be respectively mounted on the left earlobe and the right earlobe of the human body and measure a first PPG signal from the left earlobe and a second PPG signal from the right earlobe. In this case, the first measurement part 111 and the second measurement part 112 may be manufactured in the form of a small lightweight clip so as to be stably mountable on the respective earlobes.

The third measurement part 113 and the fourth measurement part 114 may be respectively mounted on an end of any one of the left fingers and an end of any one of the right fingers of a human body and measure PPG signals. The third measurement part 113 and the fourth measurement part 114 may be configured in the form of a clip as shown in FIGS. 2 and 5.

The fifth measurement part 115 and the sixth measurement part 116 may be respectively mounted on the left toe and the right toe of a human body and measure PPG signals. More specifically, the fifth measurement part 115 and the sixth measurement part 116 may be configured in the form of a large clip mountable to the respective toe parts of the human body. That is, as shown in FIG. 6, the fifth measurement part 115 and the sixth measurement part 116 in the form of the clip may be respectively mounted on the left toes and the right toes of the human body and measure a fifth PPG signal from the left toes and a sixth PPG signal from the right toes.

In this case, the fifth measurement part 115 and the sixth measurement part 116 may be configured to include a clip having a size larger than the first measurement part 111 and the fourth measurement part 114 and having a longer distance between a light emitting part and a light receiving part so that the big toes are to be stably gripped. In accordance with the exemplary embodiment, as shown in FIG. 6, the fifth measurement part 115 and the sixth measurement part 116 may be configured in the form of a clip having a width of 6 cm or more and 15 cm or less so as to enable gripping five adult toes at the same time. In addition, a toe part having a thickness of up to 5 cm may be gripped, but considering that the respective thicknesses of the five toes differ from each other, a hinge part may be flexibly configured to be mounted and fixed even in a state where the thickness of one side of the big toe and the thickness of the other side of the pinky toe are different from each other.

The analysis part 120 may perform a comparative analysis of the six PPG signals each measured by the measurement part 110. More specifically, the analysis part 120 may comparatively analyze waveforms of the six PPG signals measured by the first measurement part 111 to the sixth measurement part 116 so as to analyze a blood vessel state and blood circulation for each part of the body. In addition, the analysis part 120 may analyze degrees of time delay between the PPG waveforms measured in the first measurement part 111 to the sixth measurement part 116 to measure the blood circulation states of a patient whose blood circulation of the extremities is problematic.

In a case of electrocardiograms, two or more electrodes are connected around the heart, and the electrocardiograms are measured by using potential differences. However, PPG signals measured by the pulse oximeter may measure oxygen saturation or the like with a single channel alone. In the present disclosure, since the PPG signals are measured in six channels, which are the first measurement part 111 to the sixth measurement part 116, an independent oxygen saturation value at each measured body part may be determined.

FIG. 7 is a view illustrating a process by which the analysis part 120 performs a comparative analysis of PPG signals in the multi-channel pulse oximeter system 100 according to the exemplary embodiment of the present disclosure. As shown in FIG. 7, the multi-channel pulse oximeter system 100 according to the exemplary embodiment of the present disclosure may synchronize respective measurement times of the first PPG signal (from the left earlobe, LE), the second PPG signal (from the right earlobe, RE), the third PPG signal (from the left fingertip, LF), the fourth PPG signal (from the right fingertip, RF), the fifth PPG signal (from the left toe, LT), and the sixth PPG signal (from the right toe, RT), which are respectively measured by the first measurement part 111 to the sixth measurement part 116, and analyze degrees of time delay between PPG waveforms. In FIG. 7, the degrees of time delay analyzed by the analysis part 120 are indicated by red and green arrows, and in this case, the unit of time delay may be milliseconds (msec). For example, as shown in the red arrows shown in FIG. 7, respective degrees of time delay until peaks of the third PPG signal, the fourth PPG signal, the fifth PPG signal, and the sixth PPG signal may be calculated on the basis of a peak of the first or second PPG signal measured on the earlobes. In addition, a degree of time delay between the third PPG signal and the fourth PPG signal, a degree of time delay between the fourth PPG signal and the fifth PPG signal, etc. may be variously analyzed. Such time delay is caused by respectively different distances from the heart to the earlobes, fingertips, and toes, but the degrees of time delay become different from each other because blood circulation varies depending on blood vessel states, blood vessel elasticity, etc. Accordingly, by analyzing the degrees of time delay, the blood circulation according to the blood vessel states and blood vessel elasticity may be identified.

The result provision part 130 may provide analysis results of the analysis part 120. In this case, the result provision part 130 may quantify the analysis results of the analysis part 120 and accordingly provide, in numbers, the blood vessel states, blood vessel elasticity, and/or resultant blood circulation of a human body. A user may check and utilize the analysis results and the like provided by the result provision part 130 through electronic devices, such as a monitoring device, a computer, and a mobile terminal, that interwork with the multi-channel pulse oximeter system 100 according to the exemplary embodiment of the present disclosure.

Here, the electronic devices may include at least one of a smartphone, a tablet, a personal computer (PC), a mobile phone, a video phone, an e-book reader, a desktop PC, a laptop PC, a netbook computer, a workstation, a server, a personal digital assistant (PDA), a media box, a game console, an electronic dictionary, or wearable devices. The wearable devices may include at least one of an accessory type device (e.g., a watch, a ring, a bracelet, an anklet, a necklace, glasses, contact lenses, or a head-mounted device (HMD), a textile or clothing integral type device (e.g., electronic clothing), a body attachment type device (e.g., a skin pad or tattoo), or a bio-implantable circuit. In various exemplary embodiments, the electronic devices are not limited to the devices described above, and may be a combination of two or more of the various devices described above.

More specifically, the analysis part 120 may analyze the degrees of time delay between the PPG waveforms measured in the first measurement part 111 to the sixth measurement part 116, so as to measure blood circulation states of the patient whose blood circulation of the extremities is problematic. In addition, the result provision part 130 may provide blood circulation scores obtained by scoring the patient's blood circulation states measured by the analysis part 120. In this case, the blood circulation scores for respective parts of the left hand, the right hand, the left foot, and the right foot may be provided.

The extremities of a human body, such as hands and feet, are weak in blood circulation, and when the blood circulation in the extremities of a diabetic patient and others is problematic, there is a possibility of developing complications such as ulceration, so continuous monitoring and systematic management are required. According to the multi-channel pulse oximeter system 100 according to the exemplary embodiment of the present disclosure, since respective PPG signals are measured in six places of both earlobes, both fingertips, and both toes, so as to analyze the degrees of time delay, blood circulation in the extremities of the human body, such as the hands and the feet, may be identified individually, whereby blood circulation in each part, which is important for the diabetic patient, may be monitored. In addition, the blood circulation scores obtained by scoring the patient's blood circulation states are provided for the respective parts of the left hand, right hand, left foot, and right foot, so that the blood circulation states may be easily identified and managed without professional knowledge.

In addition, the analysis part 120 may compare PPG waveforms measured by the fifth measurement part 115 and the sixth measurement part 116 with PPG waveforms measured by the first measurement part 111 to the fourth measurement part 114, analyze the degrees of time delay, and measure blood circulation speeds of the lower extremities. The result provision part 130 may calculate and provide a varicose veins index by using the blood circulation speeds of the lower extremities measured by the analysis part 120. In this case, a varicose veins index may be provided for each part of the left foot and the right foot.

Varicose veins are abnormalities in blood circulation in which blood flows backward due to damage to valves in the lower extremity veins. When the varicose veins of the patient are not severe, the symptoms are alleviated and the swelling goes down just by the patient lying down and raising the legs higher than the heart without special treatment, but in severe cases, veins may bulge out of the skin and skin ulcers may occur, whereby medications, laser treatment, surgery, etc. may be required for the patient. Accordingly, it is required to detect varicose veins early and respond to the abnormalities appropriately.

According to the multi-channel pulse oximeter system 100 according to the exemplary embodiment of the present disclosure, respective PPG signals may be measured in six places of both earlobes, both fingertips, and both toes, and may be analyzed to determine blood circulation speeds of the lower extremities. Such blood circulation speeds in the lower extremities may be calculated, as a varicose veins index, and provided for each of the left and right feet, thereby detecting varicose veins early and responding to the abnormalities without professional knowledge.

In addition, since the multi-channel pulse oximeter system 100 according to the exemplary embodiment of the present disclosure continuously measures biometric information through the measurement part 110, a blood circulation change according to a condition change may be measured by performing an action to get up after lying down in a state of measuring respective PPG signals after wearing the measurement part 110 on each of both earlobes, both fingers, and both toes. Therefore, it may also be used for the diagnosis of orthostatic hypotension.

As described above, according to the present disclosure, the proposed multi-channel pulse oximeter system 100 may measure the PPG signals in six places on a human body, including both earlobes, both fingers and both feet, in the light transmission method, comparatively analyze the waveforms of the measured six PPG signals, and analyze the blood vessel state and blood circulation for each part of the body.

In addition, according to the present disclosure, the proposed multi-channel pulse oximeter system may measure and monitor blood circulation states of the diabetic patient whose blood circulation of the extremities is problematic by analyzing the degrees of time delay between the measured six PPG signals, prevent varicose veins by measuring the blood circulation speeds of the lower extremities, and be utilized in the diagnosis of orthostatic hypotension by measuring and analyzing the six PPG signals according to condition changes.

Meanwhile, the embodiment of the present disclosure may include a computer-readable medium including program instructions for performing operations implemented in various communication terminals. For example, the computer-readable media may include hardware devices, which are specially configured to store and execute program instructions, that include: magnetic media such as hard disks, floppy disks, and magnetic tapes; optical media such as CD-ROMs and DVDs; magneto-optical media such as floptical disks; and memories such as ROMs, RAMs, and flash memories.

As such, the computer-readable media may include program instructions, data files, data structures, and the like individually or in combination thereof. In this case, the program instructions recorded on the computer-readable media may be specially designed and configured to implement the embodiment of the present disclosure, or may be known and available to those skilled in the art of computer software. For example, the computer instructions may include not only machine language code such as one generated by a compiler, but also high-level language code executable by a computer using an interpreter or the like.

The above description of the present disclosure is for illustration, and it will be understood that those skilled in the art to which the present disclosure pertains may easily transform the present disclosure in other specific forms without departing from the technical spirit or essential features thereof. Therefore, it should be understood that the above-described exemplary embodiments are illustrative in all respects and not restrictive. For example, each component described as a single type may be implemented in a distributed manner, and similarly, components described as distributed may be implemented in a combined form.

The scope of the present disclosure is indicated by the following claims rather than the above detailed description, and all changes or modifications derived from the meaning and scope of the claims and equivalent concepts should be interpreted as being included in the claims of the present disclosure.

What is claimed is:

1. A multi-channel pulse oximeter system comprising:

a measurement part including six photoplethysmography (PPG) sensors configured to measure PPG signals in a light transmission method at both earlobes, both fingers, and both feet of a human body;

an analysis part comprising a processor configured to synchronize the six PPG signals, calculate time delays among the waveforms, and analyze blood circulation characteristics of each corresponding body part based on the calculated time delays; and a result provision part comprising a display or communication module configured to provide quantitative and graphical analysis results including blood vessel state and blood circulation information derived by the analysis part.

2. The multi-channel pulse oximeter system of claim 1, wherein the first and second PPG sensors are configured in the form of earlobe clips mountable on the respective earlobes.

3. The multi-channel pulse oximeter system of claim 1, wherein the fifth and sixth PPG sensors are configured in the form of large toe clips mountable on the respective toes.

4. The multi-channel pulse oximeter system of claim 1, wherein the processor is configured to comparatively analyze waveforms of the six PPG signals and evaluate a blood vessel state and a blood circulation condition for each of the earlobes, fingers, and feet.

5. The multi-channel pulse oximeter system of claim 4, wherein the processor calculates degrees of time delay ($\Delta t$) between peaks of the PPG waveforms measured at the six positions, and determines blood circulation states of extremities having poor blood flow based on the calculated delays.

6. The multi-channel pulse oximeter system of claim 5, wherein the display or communication module provides a numerical blood circulation score obtained by scoring the blood circulation state analyzed by the processor for each of the earlobes, fingers, and feet.

7. The multi-channel pulse oximeter system of claim 4, wherein the processor compares PPG waveforms measured at the fifth and sixth PPG sensors with those measured at the first to fourth PPG sensors (earlobes and fingers), analyzes the degrees of time delay, and calculates blood circulation speeds of the lower extremities.

8. The multi-channel pulse oximeter system of claim 7, wherein the processor calculates and the display provides a varicose vein index derived from the blood circulation speeds of the lower extremities, enabling early detection of venous valve dysfunction.

* * * * *